(12) United States Patent
Drake et al.

(10) Patent No.: US 9,636,499 B2
(45) Date of Patent: May 2, 2017

(54) LEAD DELIVERY DEVICE AND METHOD

(75) Inventors: Ronald Alan Drake, Saint Louis Park, MN (US); Stanten C. Spear, Arden Hills, MN (US); Gary Fiedler, Forest Lake, MN (US); Patrick Senarith, Circle Pines, MN (US); Lindsey Marie Tobin, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1874 days.

(21) Appl. No.: 12/183,401

(22) Filed: Jul. 31, 2008

(65) Prior Publication Data

US 2009/0326629 A1 Dec. 31, 2009

(51) Int. Cl.
| | |
|---|---|
| A61N 1/05 | (2006.01) |
| A61M 25/10 | (2013.01) |
| A61B 17/00 | (2006.01) |
| A61B 17/22 | (2006.01) |
| A61M 25/09 | (2006.01) |

(52) U.S. Cl.
CPC ......... A61N 1/056 (2013.01); A61M 25/1002 (2013.01); *A61B 2017/00243* (2013.01); *A61B 2017/22047* (2013.01); *A61B 2017/22048* (2013.01); *A61M 25/09* (2013.01); *A61N 2001/0585* (2013.01)

(58) Field of Classification Search
USPC ....................................................... 607/122
See application file for complete search history.

(56) References Cited

U.S. PATENT DOCUMENTS

| | | |
|---|---|---|
| 4,215,703 A | 8/1980 | Willson |
| 4,497,326 A | 2/1985 | Curry |
| 4,619,246 A | 10/1986 | Molgaard-Nielsen et al. |
| 5,125,904 A | 6/1992 | Lee |
| 5,147,377 A | 9/1992 | Sahota |
| 5,167,239 A | 12/1992 | Cohen et al. |
| 5,181,911 A | 1/1993 | Shturman |

(Continued)

FOREIGN PATENT DOCUMENTS

| | | |
|---|---|---|
| EP | 0 861 676 A2 | 9/1998 |
| EP | 2197540 A1 | 6/2010 |

(Continued)

OTHER PUBLICATIONS (PCT/US2009/050783) PCT Notification of Transmittal of the International Search Report and the Written Opinion of the International Searching Authority, 15 pages, Mar. 3, 2010.

(Continued)

*Primary Examiner* — Erica Lee
(74) *Attorney, Agent, or Firm* — Carol F. Barry

(57) ABSTRACT

A medical apparatus includes a guidewire and a fixator catheter. The fixator catheter comprises a tubular body with a distal portion and a proximal portion, and further includes a distal opening, a fixator secured to the distal portion, and a body opening arranged between the fixator and the proximal portion. The guidewire passes through the body opening and the distal opening of the fixator catheter. The fixator is movable between a compact configuration and an expanded configuration and, in the expanded condition, is capable of anchoring the guidewire and fixator catheter in a lumen of a blood vessel.

29 Claims, 14 Drawing Sheets

(56) References Cited

U.S. PATENT DOCUMENTS

| | | | |
|---|---|---|---|
| 5,224,491 A | 7/1993 | Mehra | |
| 5,265,622 A | 11/1993 | Barbere | |
| 5,279,299 A | 1/1994 | Imran | |
| 5,295,958 A | 3/1994 | Shturman | |
| 5,312,355 A | 5/1994 | Lee | |
| 5,364,340 A | 11/1994 | Coll | |
| 5,409,463 A | 4/1995 | Thomas et al. | |
| 5,437,083 A | 8/1995 | Williams et al. | |
| 5,449,372 A | 9/1995 | Schmaltz et al. | |
| 5,456,667 A | 10/1995 | Ham et al. | |
| 5,456,705 A | 10/1995 | Morris | |
| 5,474,563 A | 12/1995 | Myler et al. | |
| 5,549,553 A | 8/1996 | Ressemann et al. | |
| 5,653,684 A | 8/1997 | Laptewicz et al. | |
| 5,693,014 A | 12/1997 | Abele et al. | |
| 5,735,869 A * | 4/1998 | Fernandez-Aceytuno | ... 606/194 |
| 5,741,320 A | 4/1998 | Thornton et al. | |
| 5,803,928 A | 9/1998 | Tockman et al. | |
| 5,833,707 A | 11/1998 | McIntyre et al. | |
| 5,902,331 A | 5/1999 | Bonner et al. | |
| 5,954,761 A | 9/1999 | Machek et al. | |
| 5,957,903 A | 9/1999 | Mirzaee et al. | |
| 6,010,498 A | 1/2000 | Guglielmi | |
| 6,014,589 A | 1/2000 | Farley et al. | |
| 6,033,413 A * | 3/2000 | Mikus et al. ................. | 606/108 |
| 6,122,552 A | 9/2000 | Tockman et al. | |
| 6,152,946 A | 11/2000 | Broome et al. | |
| 6,161,029 A | 12/2000 | Spreigl et al. | |
| 6,196,230 B1 | 3/2001 | Hall et al. | |
| 6,322,559 B1 | 11/2001 | Daulton et al. | |
| 6,331,190 B1 | 12/2001 | Shokoohi et al. | |
| 6,415,187 B1 | 7/2002 | Kuzma et al. | |
| 6,416,510 B1 | 7/2002 | Altman et al. | |
| 6,428,489 B1 * | 8/2002 | Jacobsen et al. ............. | 600/585 |
| 6,595,989 B1 | 7/2003 | Schaer | |
| 6,602,271 B2 | 8/2003 | Adams et al. | |
| 6,662,045 B2 | 12/2003 | Zheng et al. | |
| 6,697,677 B2 | 2/2004 | Dahl et al. | |
| 6,928,313 B2 | 8/2005 | Peterson | |
| 6,931,286 B2 | 8/2005 | Sigg et al. | |
| 6,970,742 B2 | 11/2005 | Mann et al. | |
| 7,037,290 B2 * | 5/2006 | Gardeski et al. .......... | 604/95.01 |
| 7,107,105 B2 | 9/2006 | Bjorklund et al. | |
| 7,171,275 B2 | 1/2007 | Hata et al. | |
| 7,344,557 B2 | 3/2008 | Yadin | |
| 7,765,014 B2 | 7/2010 | Eversull et al. | |
| 7,976,551 B1 | 7/2011 | Gutfinger et al. | |
| 8,229,572 B2 | 7/2012 | Drake et al. | |
| 8,394,079 B2 | 3/2013 | Drake et al. | |
| 8,920,432 B2 | 12/2014 | Drake et al. | |
| 2002/0077686 A1 | 6/2002 | Westlund et al. | |
| 2002/0147487 A1 | 10/2002 | Sundquist et al. | |
| 2002/0173835 A1 | 11/2002 | Bourang et al. | |
| 2003/0028234 A1 * | 2/2003 | Miller et al. ................. | 623/1.11 |
| 2003/0088194 A1 | 5/2003 | Bonnette et al. | |
| 2003/0120208 A1 * | 6/2003 | Houser ..................... | A61F 2/95 604/103.04 |
| 2003/0204231 A1 | 10/2003 | Hine et al. | |
| 2003/0225434 A1 | 12/2003 | Glantz et al. | |
| 2003/0229386 A1 * | 12/2003 | Rosenman et al. ........... | 607/116 |
| 2004/0059348 A1 | 3/2004 | Geske et al. | |
| 2004/0116878 A1 | 6/2004 | Byrd et al. | |
| 2004/0162599 A1 | 8/2004 | Kurth | |
| 2004/0215298 A1 | 10/2004 | Richardson et al. | |
| 2005/0089655 A1 * | 4/2005 | Lim ........................... | 428/34.1 |
| 2005/0113862 A1 | 5/2005 | Besselink et al. | |
| 2005/0215990 A1 | 9/2005 | Govari | |
| 2006/0106445 A1 | 5/2006 | Woollett | |
| 2006/0210605 A1 * | 9/2006 | Chang et al. ................. | 424/434 |
| 2006/0241737 A1 * | 10/2006 | Tockman et al. ............. | 607/126 |
| 2006/0292912 A1 | 12/2006 | Bjorklund et al. | |
| 2007/0016240 A1 * | 1/2007 | Warnack et al. ............. | 606/192 |
| 2007/0043413 A1 | 2/2007 | Eversull et al. | |
| 2007/0079511 A1 | 4/2007 | Osypka | |
| 2007/0100409 A1 | 5/2007 | Worley et al. | |
| 2007/0100410 A1 * | 5/2007 | Lamson et al. ............... | 607/119 |
| 2007/0250144 A1 | 10/2007 | Falk et al. | |
| 2008/0021336 A1 | 1/2008 | Dobak, III | |
| 2008/0065013 A1 * | 3/2008 | Goodin ..................... | 604/103.09 |
| 2008/0103537 A1 | 5/2008 | Sigg et al. | |
| 2008/0103575 A1 | 5/2008 | Gerber | |
| 2008/0183255 A1 * | 7/2008 | Bly et al. ...................... | 607/116 |
| 2008/0300664 A1 | 12/2008 | Hine et al. | |
| 2009/0143768 A1 | 6/2009 | Parodi et al. | |
| 2009/0326551 A1 | 12/2009 | Drake et al. | |
| 2009/0326629 A1 | 12/2009 | Drake et al. | |
| 2009/0326630 A1 | 12/2009 | Tobin et al. | |
| 2010/0016863 A1 | 1/2010 | Drake et al. | |
| 2010/0016864 A1 | 1/2010 | Drake et al. | |
| 2010/0036473 A1 * | 2/2010 | Roth .......................... | 623/1.11 |
| 2015/0174394 A1 | 6/2015 | Drake et al. | |

FOREIGN PATENT DOCUMENTS

| | | |
|---|---|---|
| EP | 2344236 A2 | 7/2011 |
| WO | WO 2004/026371 A2 | 4/2004 |
| WO | WO 2005/053784 A2 | 6/2005 |
| WO | WO 2008/101078 A2 | 8/2008 |
| WO | WO 2009/158444 A1 | 12/2009 |
| WO | WO 2010/014413 A2 | 2/2010 |
| WO | WO 2010/014413 A3 | 4/2010 |
| WO | WO 2010/138648 A1 | 12/2010 |

OTHER PUBLICATIONS

International Search Report and Written Opinion for PCT patent application PCT/US2009/048542, Sep. 30, 2009; 13 pages.

International Search Report and Written Opinion for PCT patent application PCT/US2010/036280, Aug. 27, 2010; 9 pages.

* cited by examiner

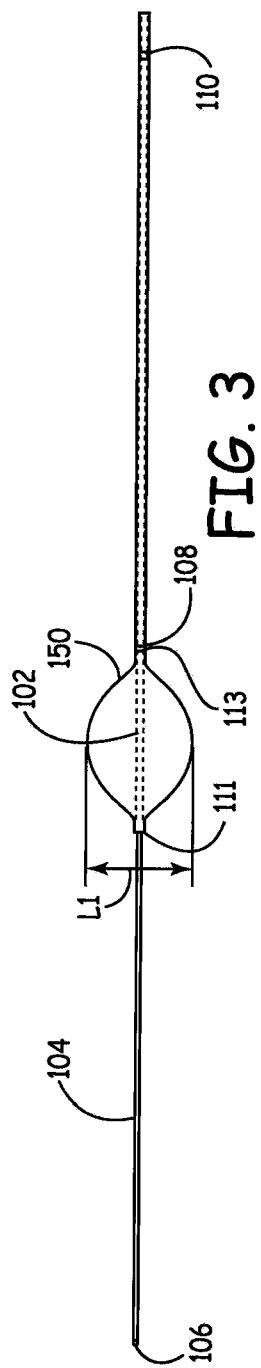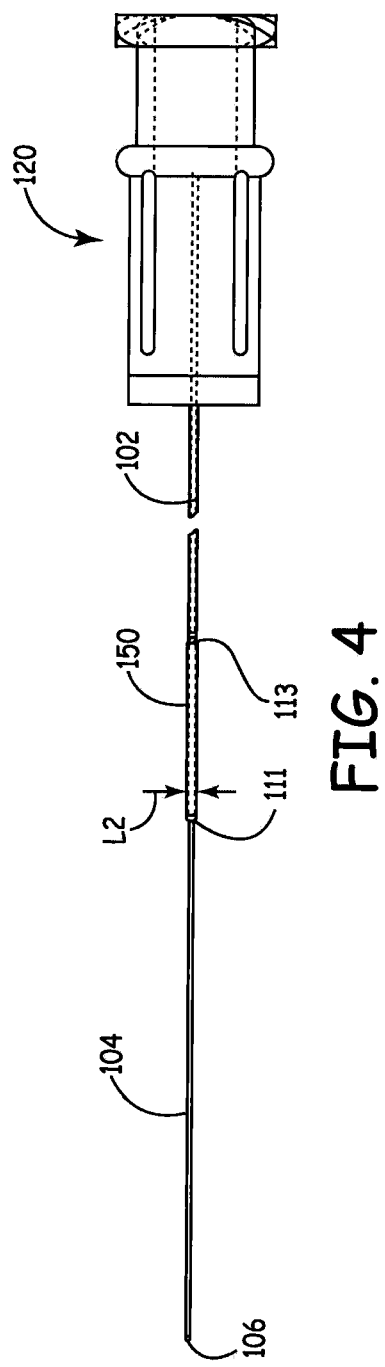

LEAD DELIVERY DEVICE AND METHOD

CROSS-REFERENCE TO RELATED APPLICATIONS

This application is related to U.S. patent application Ser. No. 11/468,910 filed on Aug. 31, 2006, which is a division of U.S. patent application Ser. No. 10/254,196, filed on Sep. 24, 2002, now U.S. Pat. No. 7,107,105.

The disclosures of the above applications are incorporated herein by reference.

INTRODUCTION

Various cardiac devices providing electrical stimulation, rhythm management, or resynchronization therapy to the heart include implantable electrically conductive leads in contact with excitable heart or other body tissue.

The present teachings provide a device and method for delivering an implantable electrically conductive lead to a target site for a use with a cardiac device.

SUMMARY

The present teachings provide a medical apparatus that includes an implantable electrically conductive lead for a cardiac device, the lead having an internal bore terminating at a distal lead opening, and a lead delivery device for delivering the distal end of the lead to a blood vessel during implantation of the lead. The lead delivery device includes a removably anchorable guidewire, and a fixator attached to a distal portion of the guidewire for anchoring the guidewire. The fixator is movable between a compact configuration and an expanded configuration. The fixator is capable of passing through the distal lead opening of the lead in the compact configuration. The fixator is capable of exerting a holding force in the range of about 0.89 to 4.45 N in the lumen of the blood vessel in the expanded configuration.

The present teachings also provide a medical method that includes inserting a distal end of cannulated catheter through cardiac tissue into a main cardiac vessel, attaching an expandable fixator to a distal portion of a guidewire, inserting the guidewire through the catheter, advancing the guidewire past the distal end of the catheter and into a target site in a lumen of a branching vessel, expanding the fixator into the target site, removably anchoring the fixator into the lumen with a holding force in the range of about 0.89 to 4.45 N, and removing the catheter. The method further includes advancing an implantable electrically conductive lead of a cardiac device over the guidewire to the target site without moving the guidewire while tensioning the guidewire, and delivering the distal portion of the lead at the target site.

In another aspect, the present teachings provide a medical apparatus that includes a cardiac device for providing cardiac therapy, or cardiac sensing, or a combination thereof, an implantable electrically conductive lead having proximal and distal ends, the proximal end couplable to the cardiac device, the lead having an internal bore terminating at a distal opening at the distal end, and a lead delivery device for delivering the distal end of the lead to a blood vessel during implantation of the lead. The lead delivery device includes a removably anchorable guidewire, and a fixator attached to a distal portion of the guidewire, the fixator movable between a compact configuration and an expanded configuration. The fixator has a compact width less or equal to about 0.483 mm and is capable of passing through the distal lead opening of the lead in the compact configuration. The fixator has an expanded width up to about 5 mm, and is capable of exerting a holding force in the range of about 0.89 to 4.45 N in the lumen of the blood vessel in the expanded configuration.

In a further aspect, the present teachings provide a medical apparatus comprising a guidewire and a fixator catheter. The fixator catheter comprises a tubular body with a distal portion and a proximal portion. The fixator catheter further comprises a distal opening, a fixator secured to the distal portion, and a body opening arranged between the fixator and the proximal portion. The guidewire is passed through the body opening and the distal opening of the fixator catheter. The fixator is movable between a compact configuration and an expanded configuration.

In yet another aspect, the present teachings provide a medical method comprising passing a guidewire through a fixator catheter. The fixator catheter comprises a tubular body with a distal portion and a proximal portion. The fixator catheter further comprises a distal opening, a fixator secured to the distal portion, and a body opening arranged between the fixator and the proximal portion. The guidewire is passed through the body opening and the distal opening of the fixator catheter. The method further comprises navigating the guidewire and fixator catheter to a desired site. At the desired site, the fixator is expanded to an expanded configuration in order to releasably secure the fixator catheter. An implantable electrically conductive lead of a cardiac device is advanced over the guidewire to the desired site while the fixator is deployed.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 3 is a plan view of a lead delivery device having a fixator according to the present teachings, the lead delivery device shown with the fixator in an expanded configuration;

FIG. 4 is a plan view of a lead delivery device having a fixator according to the present teachings, the lead delivery device shown with the fixator in a compact configuration;

DESCRIPTION OF VARIOUS ASPECTS

Figure 1:
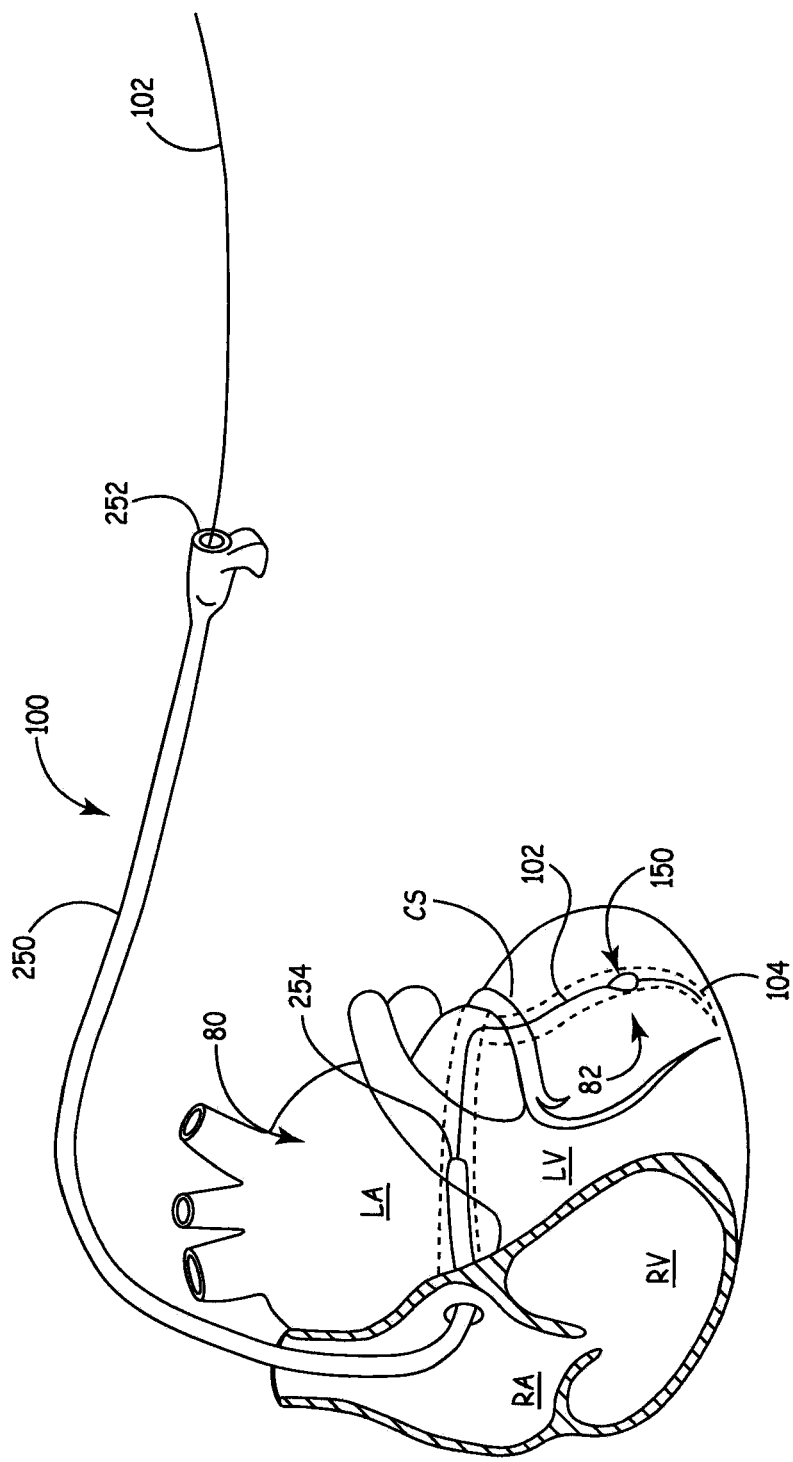
FIG. 1 is an environmental view of a lead delivery device according to various embodiments of the present teachings.

The following description is merely exemplary in nature and is in no way intended to limit the present teachings, applications, or uses. The present teachings are applicable to any devices that require implantation of electrically conductive leads, including pacemakers, defibrillators or other cardiac devices providing rhythm management, resynchronization therapy or other cardiac therapy.

During left heart (LH) lead delivery methods for implanting cardiac therapy devices, cannulated catheters can be used to provide support and stiffness and allow traceability of the lead into the coronary sinus and more acute branching vessels. For example, in Cardiac Resynchronization Therapy (CRT), a special third lead is implanted via the Coronary Sinus (CS) and positioned in a sub-selected cardiac vein to sense and/or pace the left ventricle in combination with atrial-synchronized, biventricular pacing using standard pacing technology. Following a sensed atrial contraction or atrial-paced event, both ventricles are stimulated to synchronize their contraction. The resulting ventricular resynchronization reduces mitral regurgitation and optimizes left ventricular filling, thereby improving cardiac function.

Guidewires can be used inside the Coronary Sinus and Great Cardiac Vein to gain access to acute side branches. A guidewire is placed into the targeted vessel and the lead is placed over the guidewire and through the catheter. Under existing methods, during lead delivery, a compressive force is maintained by a forward pressure on both the guidewire and lead to allow the lead to travel distally in the branching veins at the target site. The lead itself is designed to provide stiffness and steerability characteristics for the purpose of placement into the vessels. After the LH lead has reached its desired location, the delivery catheters used during the procedure must be removed by slitting because the proximal end of the lead is larger in diameter than the bore of the catheter and the catheter cannot be removed over the lead. The slitting procedure requires a very specific skill set, provides multiple avenues for user error and places constraints on catheter design, construction and use.

In contrast to the existing method described above, the present teachings provide a lead delivery device method that does not require slitting the catheter. The lead delivery device includes a guidewire that can be temporarily anchored in a sub-selected acute coronary vein branch during lead delivery. Fixation can be provided by a fixator that expands from a compact configuration of very low profile fitting inside a lead to an expanded configuration having a dimension large enough to allow sufficient tension to be placed on the guidewire to enable lead delivery over the guidewire in a zip-line or rope-climbing manner, as described below. The guidewire with the fixator in the compact configuration can be guided through the catheter to the target site. The catheter can then be removed before the lead is advanced over the guidewire. After the lead is implanted, the fixator is returned to the compact configuration and removed together with the guidewire through the implanted lead without slitting.

Figures 1A, 1B:
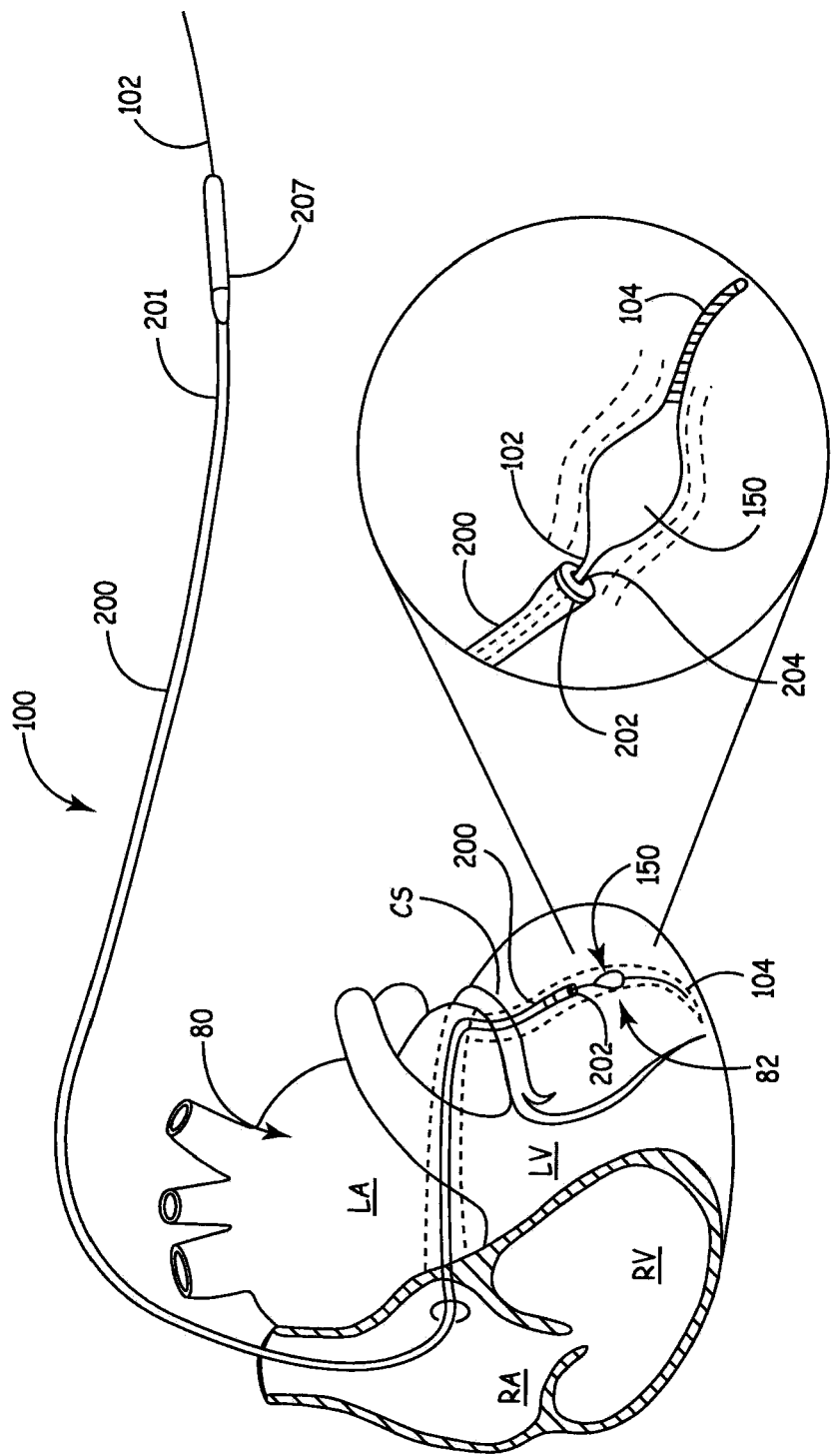
FIG. 1A is an environmental view of the lead delivery device of FIG. 1, shown in a second aspect.
FIG. 1B is an enlarged detail of the lead delivery device of FIG. 1B.
Figure 2:
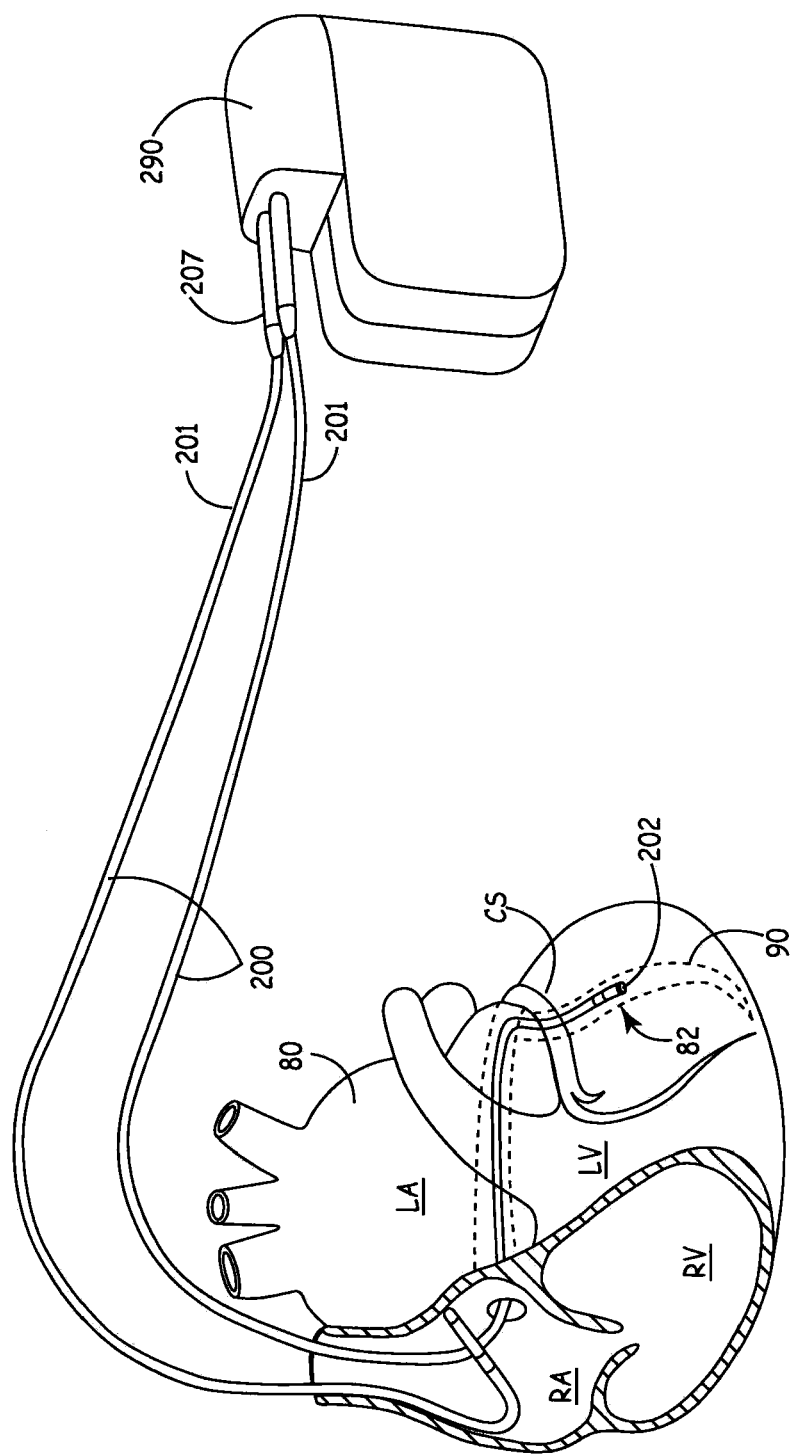
FIG. 2 is a perspective environmental view of the cardiac device with the lead implanted after the lead delivery device of FIG. 1B is removed.

An exemplary lead delivery device 100 according to the present teachings is illustrated during lead delivery of an electrically conductive lead 200 in FIGS. 1, 1A and 1B. An implanted lead 200 is shown in FIG. 2, after the lead delivery device 100 is removed. The lead 200 can be cannulated having an internal bore or lumen 204, a proximal portion 201, and a distal portion 202. The proximal portion 201 can be coupled with a connector pin 207 to a connector block of a cardiac device 290, with which the lead 200 is in electrical communication. A catheter 250 having a proximal end 252 and a distal end 254 can be used to insert the lead delivery device initially through heart tissue 80, as shown in FIG. 1.

The lead delivery device 100 can include a guidewire 102 entering a proximal end 252 of the catheter 250 and exiting through a distal end 254 of the catheter 250 as shown in FIG. 1. The guidewire 102 can be solid or cannulated with a bore 103, as shown in FIG. 12. The guidewire 102 can include a distal portion 104 terminating in a tip 106. The distal portion 104 can be flexible for ease in guiding the guidewire 102 through tortuous blood vessels to a target site 82, such as a branching vein branching off the coronary sinus or other main blood vessel. The lead delivery device 100 can include a fixator 150 coupled to the guidewire 102. The fixator 150 can assume an expanded or deployed configuration for anchoring the guidewire 102 near a target site 82 during lead delivery and implantation, as shown in FIGS. 3, and 5-11, illustrating various fixator aspects. Referring to FIG. 1, the catheter 250 can be removed by retracting the catheter 250 from heart tissue 80 after the lead delivery device is anchored at the target site 82. No slitting of the catheter 250 is required for removal of the catheter 250. After the catheter 250 is removed, the lead 200 can be guided over the guidewire 102 to the target site 82, as discussed further below.

The fixator 150 can be returned to a compact or undeployed configuration, such as the configuration illustrated in FIG. 4, for retracting and removing the guidewire 102 after lead delivery and implantation. The maximum dimension, diameter or width of the fixator 150 in the expanded configuration is denoted as L1 and in the contracted configuration as L2, as illustrated in FIGS. 3 and 4 for a fixator in the form of a balloon.

FIGS. 5-11 illustrate various fixators 150 in their expanded configuration showing the maximum dimension L1 for each fixator 150. The dimension L1 is selected to achieve a fixation force within a blood vessel of an amount that allows the guidewire 102 to be pulled in tension without being dislodged from the blood vessel while the lead is pushed over the guidewire 102, as discussed below. The fixation force F can be equal to or greater than about 2.24 N, or about 0.5 lbs, for achieving sufficient fixation within the blood vessel wall. The fixation force F can generally be in the range of about 0.89 to 4.45 N (or 0.2 to 1.0 lbs), depending on various factors, including the geometry of the branching vessel. The deployed width or dimension L1 corresponding to this fixation force F can be 5 mm, while the undeployed width or dimension L2 can be maintained to equal to or less than about 0.019 inches, or about 0.483 mm, to allow easy passage through commercially available leads, such as those used with medical devices available from Medtronic, Inc., of Minneapolis, Minn.

Figure 13:
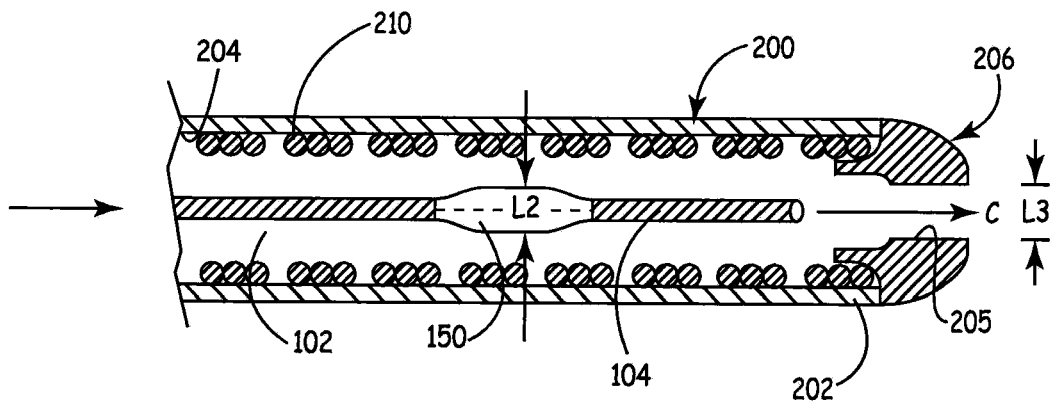
FIG. 13 is a sectional view of a lead delivery device according to the present teachings with a fixator in a compact configuration inside a lead.
Figure 14:
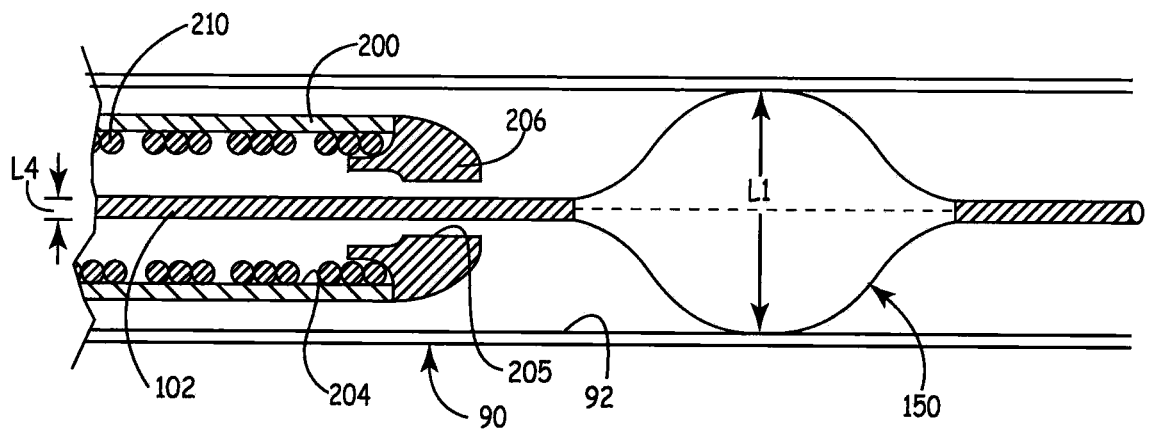
FIG. 14 is the lead delivery device of FIG. 13, shown with the fixator in an expanded configuration outside the lead.
Figure 15:
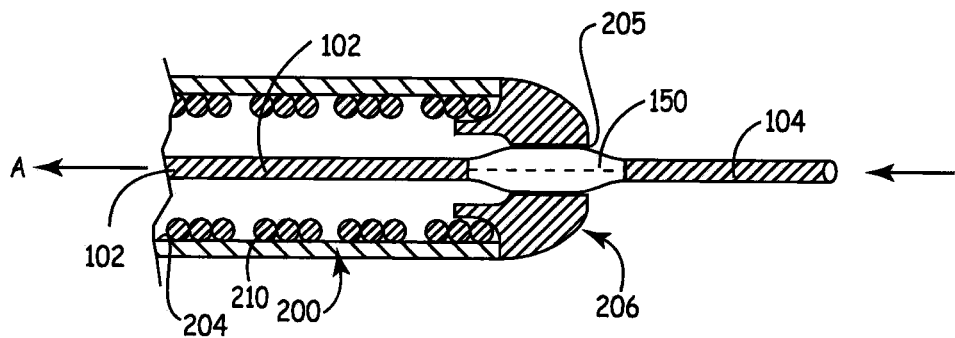
FIG. 15 is the lead delivery device of FIG. 13, shown with the fixator partially retracted inside the lead.

Referring to FIGS. 13-15, the distal portion 202 of an electrical lead 200 is illustrated in connection with a guidewire 102 having a width L4 and a fixator 150 having an undeployed width L2. The lead 200 is conductive and can deliver therapy in the form of electric energy at the target site 82. In one aspect, the lead 200 can also sense and relay information about electrical activity from the heart tissue 80 or target site 82 back to the cardiac device 290. The lead 200 can have an internal bore or lumen 204, an internal coil or other conductive element 210 and a tip portion 206 that can be an electrode tip with or without a seal. The tip portion 206 can define a distal opening 205 with width L3. In one aspect, the tip portion 206 can include a seal with flexible flaps, not shown. The guidewire width L4 can be about 0.346 mm (or about 0.014 inches) for providing steerability, stiffness and sufficient support for lead delivery over the guidewire 102.

Figure 16:
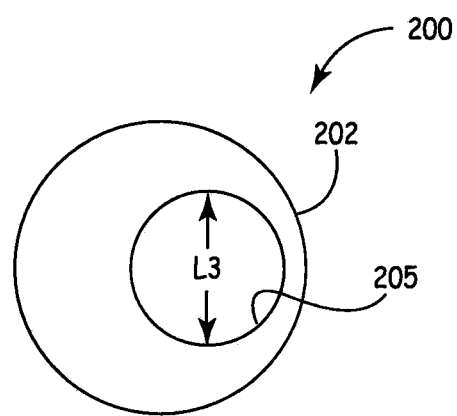
FIG. 16 is an end view of a distal end of an electrical lead with an offset distal opening.

The compact width L2 of the fixator 150 can be equal to or less than the width L3 of the distal opening 205, such that the fixator 150 can be pushed through the distal opening 205 in the direction C, as shown in FIG. 13. In one aspect the distal opening 205 can be offset relative to a central longitudinal axis of the lead 200, as shown in FIG. 16. The fixator 150 can be deployed to the expanded configuration within the blood vessel 90 such that the expanded width L1 of the fixator 150 can press against the internal lumen 92 of the blood vessel 90 with a holding force F, as discussed above, for temporarily anchoring the guidewire 102 into the blood vessel 90, as shown in FIG. 14.

Figure 5:
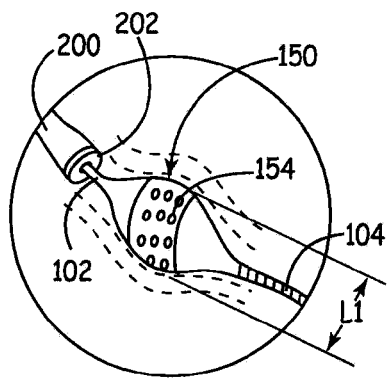
FIGS. 5-11 illustrate various fixators for a lead delivery device according to the present teachings.
Figure 7:
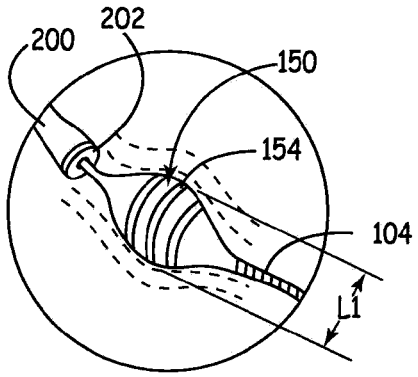

Various fixators 150 can be used to temporarily and removably anchor the guidewire 102 in the lumen 92 of a blood vessel 90. Referring to FIGS. 3 and 4, the fixator 150 can be a balloon having first and second ends 111, 113 attached to the guidewire 102. The balloon can be inflated, for example, with a gas or fluid, including a gel or other liquid, provided by a syringe through a valve 110 at a proximal end of the guidewire 102. In another aspect, a luer lock inflation port 120 can be coupled to the guidewire 102 for deploying the balloon. The balloon can be made from a polyblend material which is heated and stretched, placed around the guidewire 102 and bonded at first and second ends 111, 113 of the balloon onto the guidewire 102 with small amounts of cyanoacrylate adhesive, for example. A radio-opaque marker 108 in the form of a band can be placed adjacent the second (proximal) end 113 of the balloon for visualization during guided navigation. The radio-opaque marker 108 can also be in the form of a radio-opaque balloon coating or radio-opaque fluid filling the balloon. In another aspect, the balloon-type fixator 150 can include an etched fixation surface with etched surface fixation formations 154 in the form of bumps, rings, etc., as illustrated in FIGS. 5 and 7. In another aspect, the fixator 150 can be a balloon with spiral or helical or otherwise curved configuration for maintaining a percentage of blood flow through the blood vessel 90 and aiding fixation in tortuous anatomy.

Figure 9:
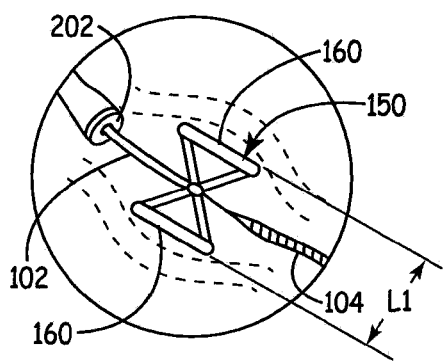
Figure 10:
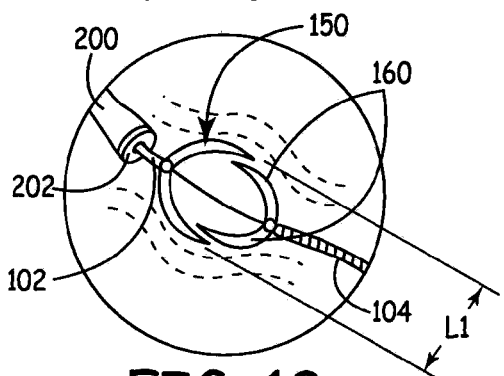
Figure 11:
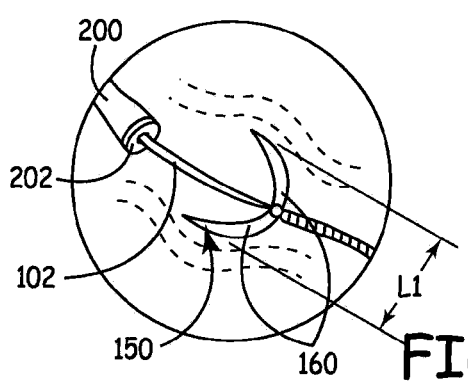
Figure 11A:
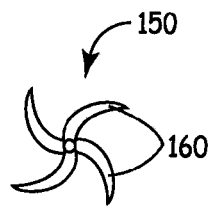
FIG. 11A is a top view of the fixator of FIG. 11.
Figure 12:
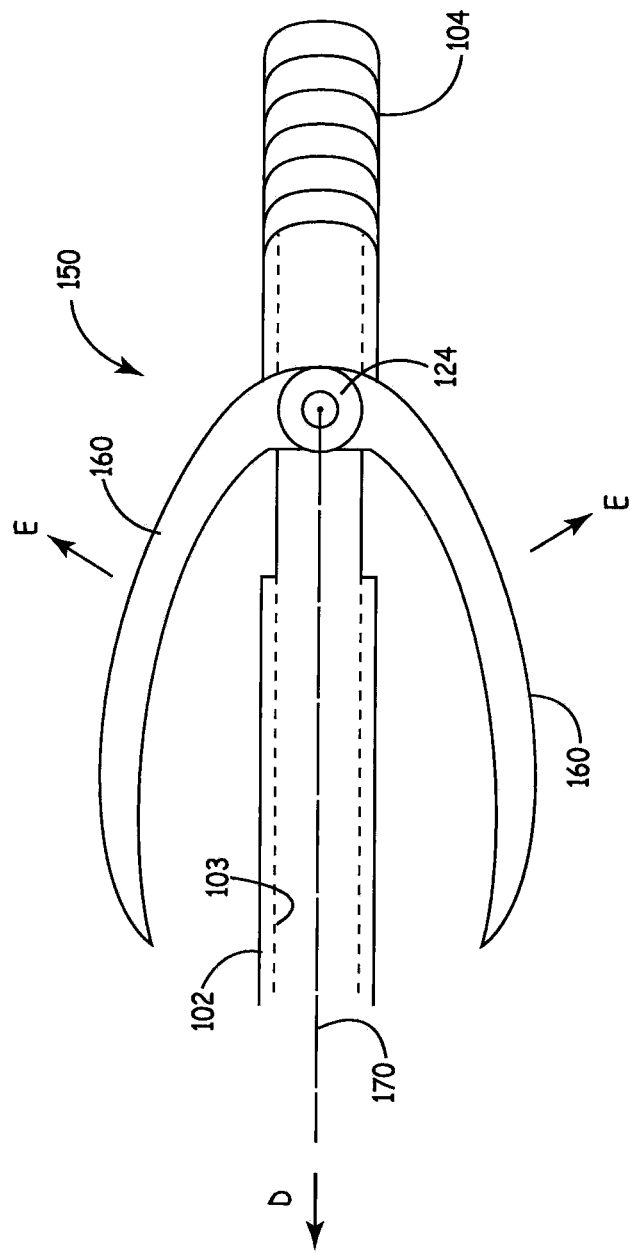
FIG. 12 is a side view of the fixator of FIG. 11, illustrating a deployment mechanism.

Referring to FIGS. 9-12, the fixator 150 can also be in the form of a mechanical anchor with deployable straight wings 160, as shown in FIG. 9, or curved wings 160, as shown in FIG. 10, or a pinwheel-type fixator 150, as shown in FIGS. 11 and 11A. The mechanical anchor 150 can be deployed with a longitudinal actuator 170 in the form of a wire or string or other elongated member passing through the bore 103 of a cannulated guidewire 102. Referring to FIG. 12, for example, the anchor wings 160 can pivot about a pivot pin 124 connected to the actuator 170 and can be deployed to the expanded position in the direction of arrows E by pulling the actuator 170 in the direction of arrow D. In other aspects, the fixator 150 can be in the form of a superelastic wire, such as nitinol, and can be pre-shaped to expand to an anchorable configuration within the blood vessel 90.

Figure 6:
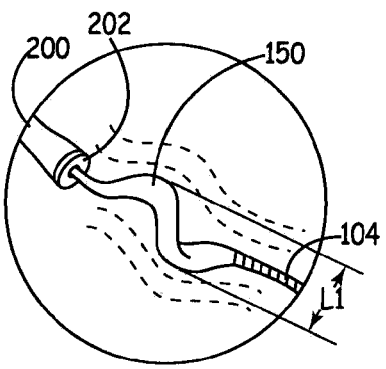
Figure 8:
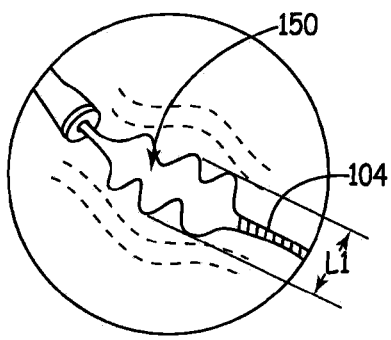

In another aspect, fixators 150 including polymer lobes or superelastic or memory-shape wire can be used. Further, the dimensions of the fixator 150, including the expanded width L1 and the compact width L2 can be selected to match the range of most common vessel sizes. The expanded shape of the fixator 150 can be selected to increase the contact area with the blood vessel and or provide multiple contact surfaces for increasing holding force and stability, as shown in FIGS. 6, 8, and 10, for example. The expanded shape can have a symmetric profile, as shown in FIG. 9, for example, or a non-symmetric profile, as shown in FIG. 6, for example. In other aspects, the expanded shape can have an asymmetric profile for anchoring unidirectionally rather than bi-directionally.

As discussed above, deployment of the fixator 150 and anchoring can occur after the cannulation of the coronary sinus CS with the catheter 250 and after sub-selection of a side branch with the guidewire 102. Further, fixation of the guidewire 102 by the expandable fixator 150 can be maintained during lead delivery and terminated after the lead 200 is delivered to the target vessel at the target site 82. At the discretion of the operating physician, fixation and release can occur multiple times during the medical procedure. Damage to the lead 200 during fixation can be avoided because fixator expansion and fixation occurs outside the lead 200.

It should be appreciated, that according to the present teachings the lead delivery device 100 with either a balloon or mechanical fixator 150 is configured and designed to function as a wedge or anchoring device for temporarily anchoring the guidewire 102 during the implantation of the electrical lead 200.

Referring to FIGS. 1-2, and 13-15, the cannulated catheter 250 can be inserted through heart tissue 80 into a coronary sinus CS, cardiac great vein or other main vessel stopping short of a target site 82 that is located in a sub-selected acute branching vessel 90. The guidewire 102 with the fixator 150 in the undeployed compact configuration can be inserted through the catheter 250, advanced past the distal end 254 of the catheter 250 through a main vessel to the target site 82 in the branching vessel 90, as shown in FIG. 1. The fixator 150 can then be deployed and become anchored in the lumen 92 of the branching vessel 90 with a holding force F, as discussed above. The catheter 250 can then be retracted and completely removed with no slitting procedure. The lead 200 can be guided over the anchored guidewire 102 until the distal portion 202 of the lead 200 reaches the target site 82, as shown in FIG. 1B. The lead 200 can be advanced by keeping the guidewire 102 in tension while pushing the lead 200 in the direction of the fixator 150. When the distal portion 202 of the lead 200 reaches the target site 82, the fixator 150 can be returned to its undeployed compact configuration and be retracted through the lumen 204 of the lead 200, as shown in FIG. 15. The lead 200 can remain installed in the target site 82, as shown in FIG. 2, or advanced more distally in the branching vessel 90 beyond the original target site 82 after the removal of the guidewire 102.

It will be appreciated that, in other aspects, the catheter 250 may be retained during the entire lead delivery procedure, such that the lead is inserted through the catheter 250 and over the guidewire 102, but in such cases slitting of the catheter 250 may not be avoided after lead implantation. In further aspects, the guidewire 102 and the lead 200 can be inserted through the catheter 250 in any order, i.e., guidewire 102 first, or lead 200 first or at the same time. In all aspects, however, the guidewire 102 can first be advanced to the target site 82 of a branching vessel 90 and the fixator 150 be deployed at the target site 82. Only then the distal portion 202 of the lead 200 is advanced to the target site 82 by pushing the lead 200 over the guidewire 102 toward the target site 82, while the guidewire 102 remains fixed. Specifically, the lead 200 can be advanced to the target site 82 in a climbing-like or zip line-like manner by pulling and tensioning the guidewire 102 while the guidewire 102 remains anchored with the deployed fixator 150 at the target site 82.

Figure 17:
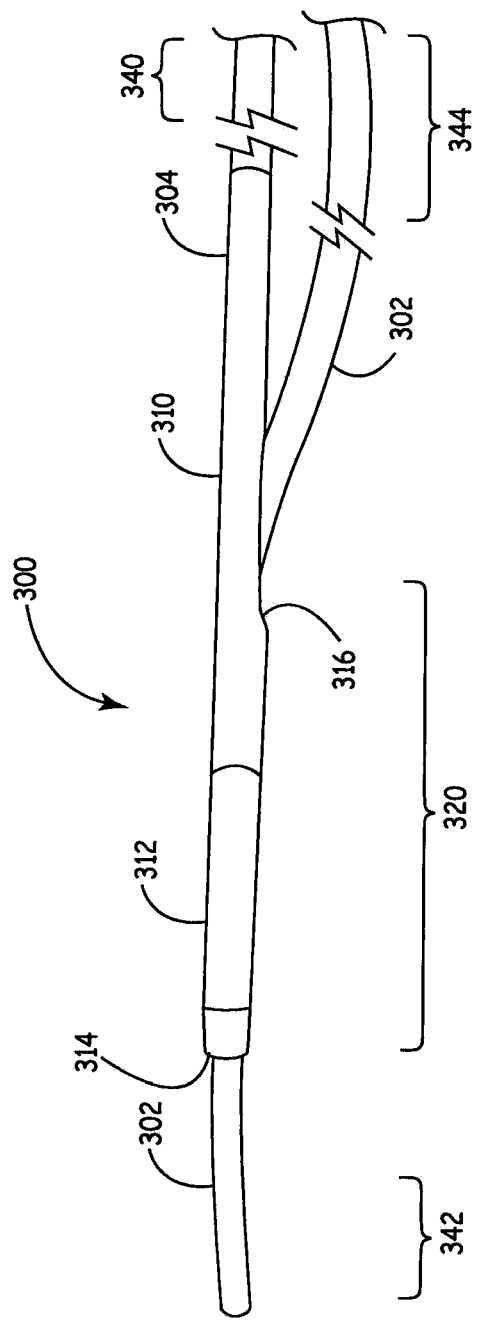
FIG. 17 is a plan view of a lead delivery device having a fixator according to the present teachings, the lead delivery device shown with the fixator in a compact configuration.

Referring now to FIG. 17, a lead delivery device 300 according to some embodiments of the present disclosure is illustrated. Lead delivery device 300 comprises a guidewire 302 and fixator catheter 304. Guidewire 302 may comprise a solid wire (as illustrated) or be cannulated, and includes proximal portion 344 and distal portion 342. The fixator catheter 304 is a cannulated catheter comprising a tubular body 310 with a distal portion 320 and proximal portion 340. A fixator 312 is secured on the distal end 320 of fixator catheter 304. In FIGS. 17-22, fixator 312 comprises an inflatable balloon, although any other form of fixator may be utilized, as described above.

Guidewire 302 passes through fixator catheter 304 such that the guidewire 302 is encased within the tubular body 310 in at least a portion of the distal portion 320 of the fixator catheter 304. In the illustrated embodiments, this is accomplished by passing the distal portion 342 of the guidewire 302 through the body opening 316 of fixator catheter 304 such that it extends through the distal opening 314. In this manner, the guidewire 302 and fixator catheter 304 are in communication at their distal portions 342, 320, while being separate at their proximal portions 344, 340.

Figure 18:
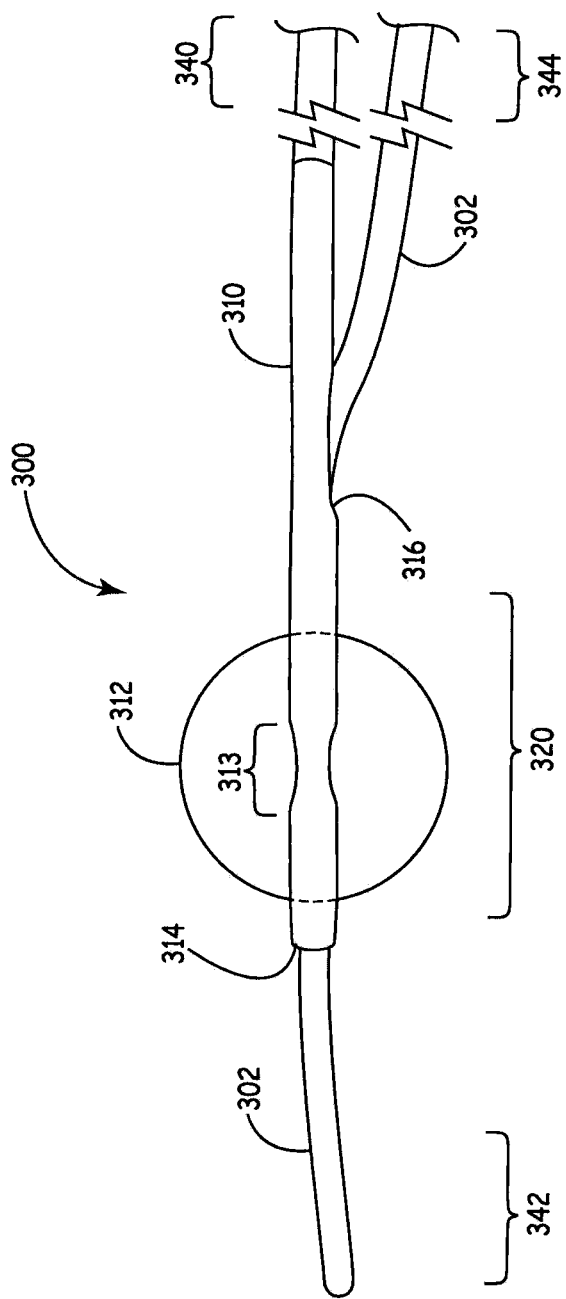
FIG. 18 is a plan view of a lead delivery device having a fixator according to the present teachings, the lead delivery device shown with the fixator in an expanded configuration.

Referring now to FIG. 18, lead delivery device 300 is shown in the condition where fixator 312 is expanded. In the illustration, fixator 312 comprises an inflatable balloon that may be expanded by a gas or fluid, as described more fully above. In some embodiments, the tubular body 310 of the fixator catheter 304 includes a lumen (not shown) that is in communication with the inflatable balloon 312 and proximal end 340. By providing a pressurized gas or fluid to the balloon 312, the fixator 312 is expanded to the expanded configuration. In the expanded configuration, the pressure inside balloon 312 will exert a force on a compressible or collapsible portion 313 of tubular body 310. In the illustrated embodiment, the compressible portion 313 is a portion of the lumen of the fixator catheter within the inflatable balloon, however, the compressible portion 313 may comprise a lumen of the balloon itself or other arrangement. The force exerted by inflatable balloon 312 on portion 313 of tubular body 310 will cause that portion 313 to compress guidewire 302 such that guidewire 302 is secured to fixator catheter 304. Portion 313 may be formed by providing a thinner wall in portion 313 than is utilized in the remainder of tubular body 310. Alternatively, portion 313 may be formed of a different material than that used to form the rest of tubular body 310, or any other alternative structure may be utilized (such as, adding a constrictive device or other securing mechanism). While the illustration in FIG. 18 shows an inflatable balloon 312 and a compressible or contract portion 313 of tubular body 310 to secure the guidewire 302 to fixator catheter 304, alternative structures and fixators may be substituted such that the guidewire 302 and fixator catheter 304 are secured together in the expanded configuration, while remaining independently movable in the compact configuration.

Figure 19:
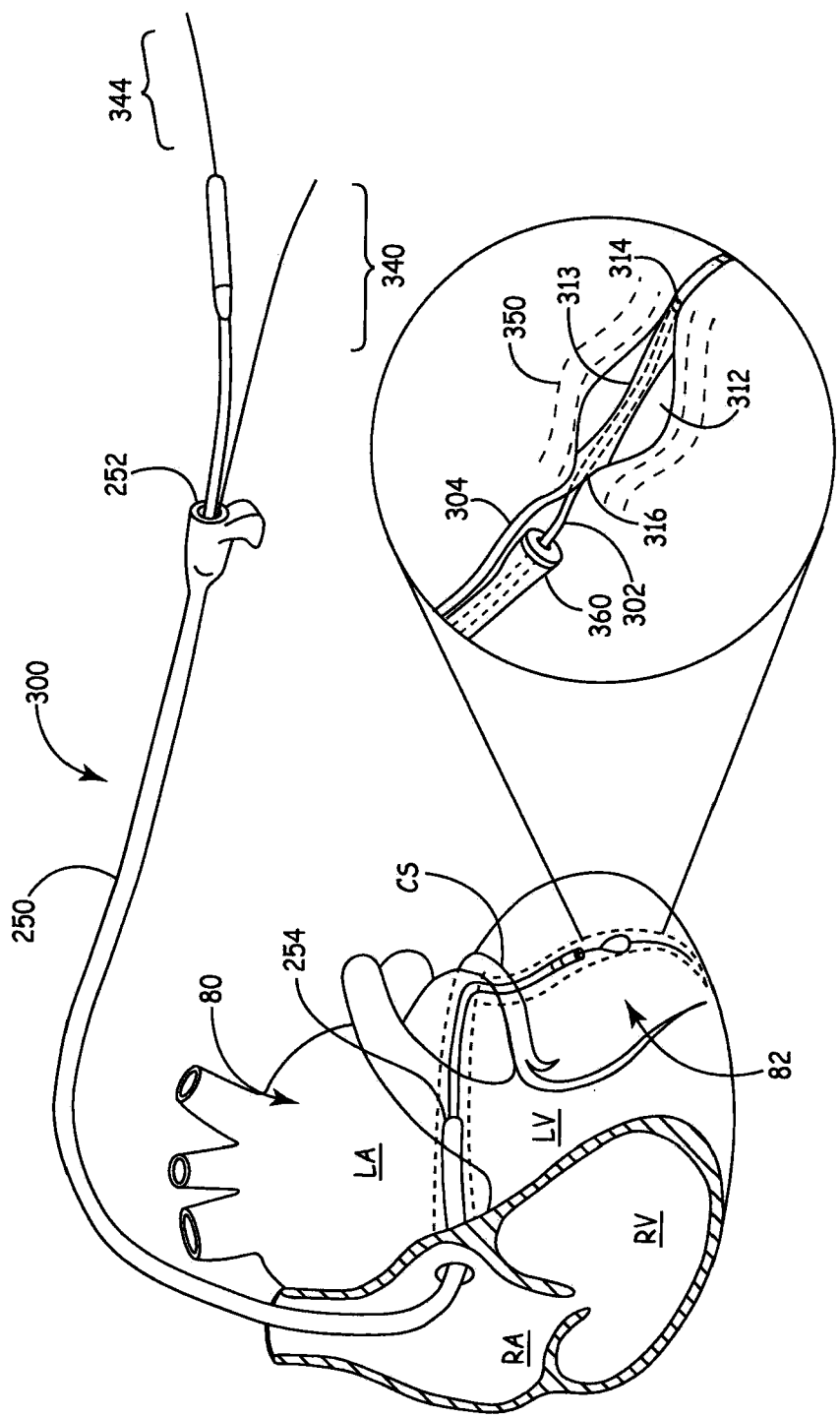
FIG. 19 is an environmental view of a lead delivery device according to various embodiments of the present teachings.
Figure 20:
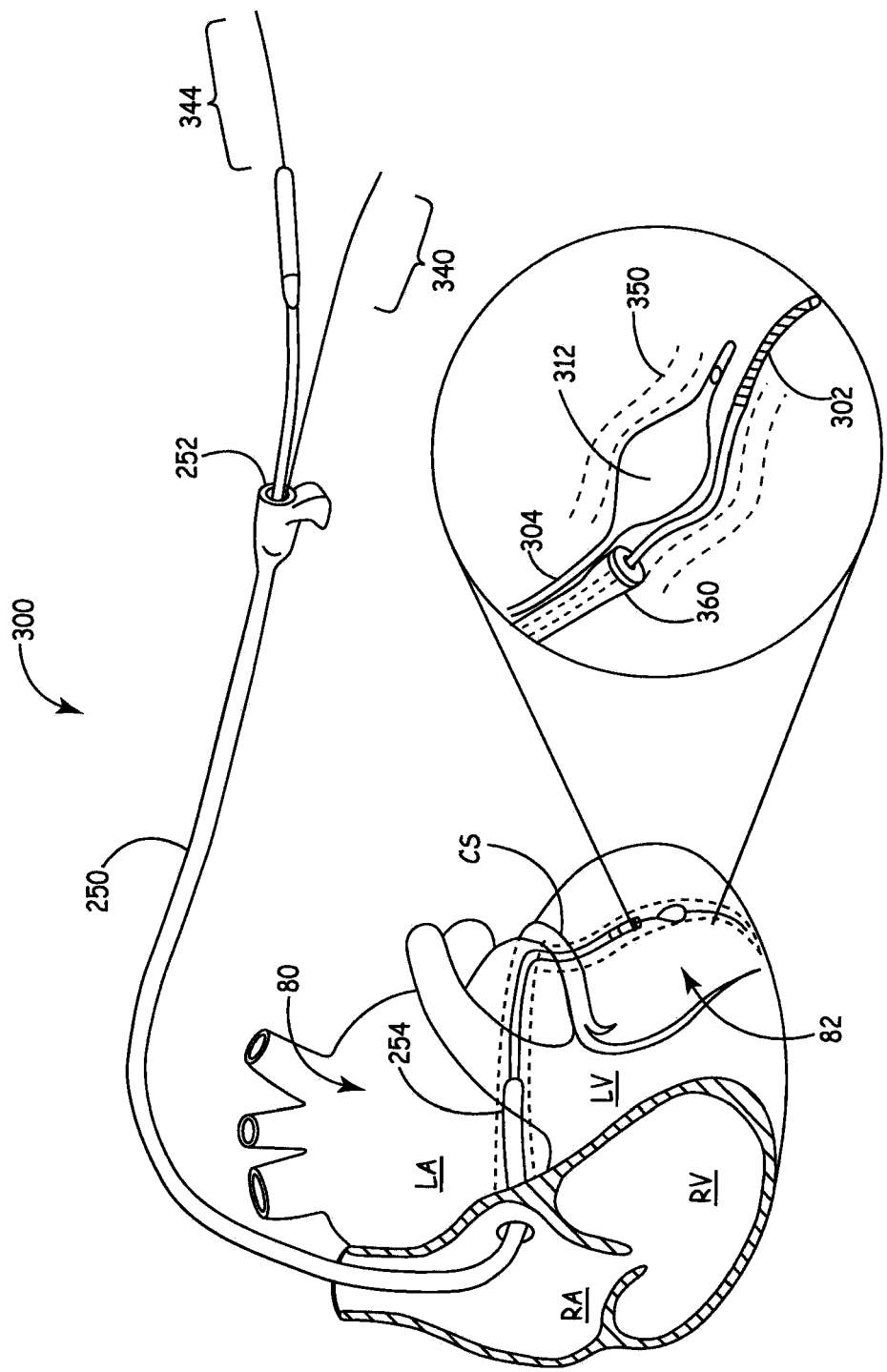
FIG. 20 is an environmental view of a lead delivery device according to various embodiments of the present teachings.

Referring now to FIGS. 19-22, a method for using lead delivery device 300 to implant an implantable electrically conductive lead 360 within a blood vessel 350 is illustrated. Similar to FIG. 1, FIGS. 19-20 show the lead delivery device 300 utilized to implant implantable electrically conductive lead 360 within the coronary sinus CS of heart tissue 80. A delivery catheter 250 having a proximal end 252 and distal end 254 may be utilized to assist in the delivery of guidewire 302 and fixator catheter 304 to a target or desired site 82. The fixator catheter 304, with guidewire 302 passed therein, is inserted through catheter 250 and navigated to a position within the desired site 82. Upon delivery to desired site 82, fixator catheter 304 deploys its fixator 312 to secure guidewire 302 and fixator catheter 304 within blood vessel 350. In the expanded configuration, fixator 312 exerts a force, as described above, upon the wall of blood vessel 350 sufficient to anchor both the guidewire 302 and fixator catheter 304 in the desired site 82 while delivery catheter 250 is removed and/or implantable electrically conductive lead 360 is delivered to desired site 82, e.g., via guidewire 302.

In the illustrations of FIGS. 19 and 20, delivery catheter 250 is shown as being present within the heart tissue 80 during delivery of lead 360. As shown in FIG. 19, in the expanded configuration fixator 312 compresses or collapses portion 313 of fixator catheter 304 such that guidewire 302 is fixedly secured within fixator catheter 304, as described more fully above. Alternatively, as shown in FIG. 20, guidewire 302 may be removed from fixator catheter 304 before fixator 312 is expanded. Fixator 312 may then be expanded to fixedly secure guidewire 302 between fixator 312 and the wall of blood vessel 350. Once guidewire 302 is fixedly secured within blood vessel 350, implantable electrically conductive lead 360 may be delivered to desired site 82 by, e.g., traveling over guidewire 302. With the guidewire 302 secured, the risk of the lead 360 being delivered incorrectly, i.e., outside of desired site 82, due to unintentional movement of guidewire 302 is reduced.

Once lead 360 is delivered to the desired site 82, the fixator 312 may be contracted to a compact configuration (as shown in FIG. 17, for example) and both guidewire 302 and fixator catheter 304 may be removed from desired site 82 and heart tissue 80. In some embodiments, fixator 312 may be utilized to secure lead 360 against blood vessel wall 350 while guidewire 302 is removed (see, e.g., FIG. 22). In this manner, it can be ensured that there is no unanticipated movement of lead 360 from desired site 82 while guidewire 302 is removed from the patient's body.

Figure 21:
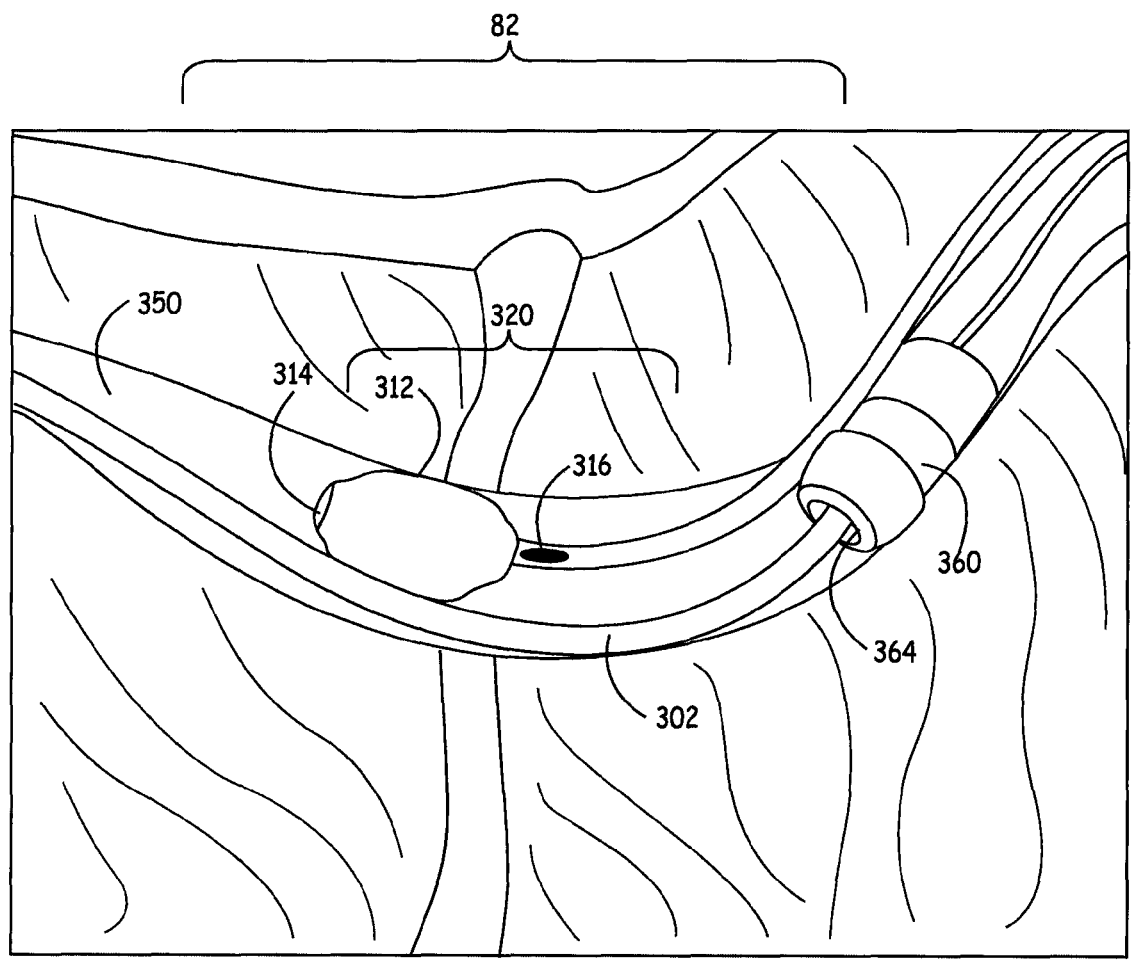
FIG. 21 is an environmental view of a lead delivery device according to various embodiments of the present teachings.
Figure 22:
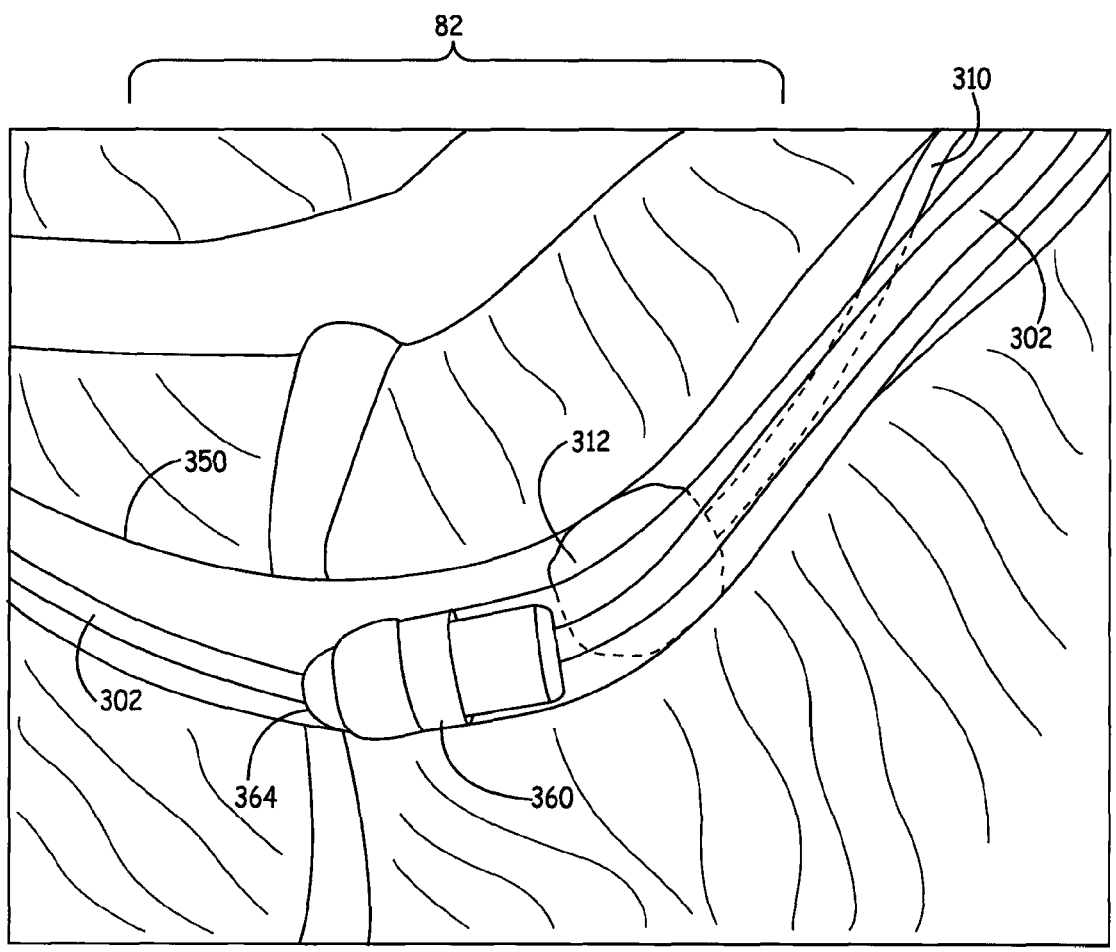
FIG. 22 is an environmental view of a lead delivery device according to various embodiments of the present teachings.

Referring now to FIGS. 21 and 22, a method of finely adjusting the position of guidewire 302 and lead 360 is illustrated. FIG. 21 shows fixator 312 in the expanded condition wherein guidewire 302 is secured between fixator 312 and the wall of blood vessel 350. This is accomplished, for example, by delivering lead delivery device 300 to the desired site 82 and then removing guidewire 302 from distal opening 314 and body opening 316 of fixator catheter 304. The guidewire 302 may be pulled out of communication with fixator catheter 304 by pushing on fixator catheter 304 until the distal portion 342 of guidewire 302 is pulled out of and exits body opening 316. Then, guidewire 302 may be pushed past the distal portion 320 of fixator catheter 304, as illustrated. Fixator 312 may be expanded to secure guidewire 302 against the wall of blood vessel 350 and implantable electrically conductive lead 360 can then be navigated to desired site 82 by, for example, traveling over guidewire 302 through opening 364.

The position of implantable electrically conductive lead 360 and guidewire 302 may be finely adjusted with the selective use of fixator catheter 304. Fixator 312 may be expanded to secure guidewire 302 (as shown in FIG. 21) such that the position of lead 360 may be adjusted. Alternatively, as shown in FIG. 22, fixator catheter 304 may be moved such that fixator 312 is immediately adjacent the body of lead 360. Fixator 312 may then be expanded to secure lead 360 within blood vessel 350. With lead 360 secured, the position of guidewire 302 may be adjusted without the possibility of moving lead 360. In this manner, a user may alternate between securing the guidewire 302 or lead 360 at a certain position, while adjusting unsecured lead 360 or guidewire 302, respectively, and thus more accurately and simply adjust the positioning of lead 360 within desired site 82.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A medical apparatus, comprising:
   a guidewire;
   a fixator catheter comprising a tubular body with a distal portion and a proximal portion, the fixator catheter further comprising a body opening and a distal opening at a distal end of the fixator catheter, wherein the body opening is defined through a portion of the tubular body of the fixator catheter to a lumen extending through the tubular body of the fixator catheter including the distal and proximal portions thereof and which lumen terminates at the distal opening, and further wherein at least a portion of the body opening is defined through the tubular body of the fixator catheter at the distal portion thereof; and
   a fixator secured to the distal portion of the fixator catheter; and wherein:
      the guidewire passes through the body opening of the fixator catheter, through a portion of the tubular body at the distal portion of the fixator catheter, and through the distal opening of the fixator catheter, and further wherein the guidewire and the fixator catheter are in communication at the distal portion of the fixator catheter with at least a portion of the guidewire extending through and within a portion of the tubular body of the fixator catheter while the guidewire is separate and outside of the tubular body of the fixator catheter at the proximal portion of the fixator catheter, and the fixator is movable between a compact configuration and an expanded configuration, wherein the fixator is configurable to secure a portion of the guidewire to the fixator catheter in the lumen within the portion of the tubular body at the distal portion of the fixator catheter in the expanded configuration.

2. The medical apparatus of claim 1, wherein the guidewire is secured to the fixator catheter when the fixator is in the expanded configuration.

3. The medical apparatus of claim 2, wherein the guidewire is movable in relation to the fixator catheter when the fixator is in the compact configuration.

4. The medical apparatus of claim 1, wherein the fixator comprises an inflatable balloon comprising etched surface fixation formations.

5. The medical apparatus of claim 1, wherein the fixator comprises an inflatable balloon comprising a helical or spiral configuration for following a tortuous path.

6. The medical apparatus of claim 1, wherein the fixator comprises a mechanical anchor having deployable parts.

7. The medical apparatus of claim 6, wherein the deployable parts comprise movable wings.

8. The medical apparatus of claim 6, wherein the fixator comprises a pinwheel.

9. The medical apparatus of claim 1, wherein the body opening is defined through the tubular body of the fixator catheter proximate the fixator.

10. A medical apparatus, comprising:
    a guidewire; and
    a fixator catheter comprising a tubular body with a distal portion and a proximal portion, the fixator catheter further comprising:
       a distal opening at a distal end of the fixator catheter;
       a fixator secured to the distal portion of the fixator catheter; and
       a body opening arranged between the fixator and the proximal portion, wherein the body opening is defined through a portion of the tubular body of the fixator catheter to a lumen extending through the tubular body of the fixator catheter including the distal and proximal portions thereof and which lumen terminates at the distal opening, and further wherein at least a portion of the body opening is defined through the tubular body of the fixator catheter at the distal portion thereof, wherein:
          the guidewire passes through the body opening of the fixator catheter, through a portion of the tubular body at the distal portion of the fixator catheter, and through the distal opening of the fixator catheter, and further wherein the guidewire and the fixator catheter are in communication at the distal portion of the fixator catheter with at least a portion of the guidewire extending through and within a portion of the tubular body of the fixator catheter while the guidewire is separate and outside of the tubular body of the fixator catheter at the proximal portion of the fixator catheter, and
          the fixator is movable between a compact configuration and an expanded configuration, wherein the fixator is configurable to secure a portion of the guidewire to the fixator catheter in the lumen within the portion of the tubular body at the distal portion of the fixator catheter in the expanded configuration; and further wherein the fixator comprises an inflatable balloon and the guidewire passes through a compressible portion of the fixator catheter within the inflatable balloon.

11. The medical apparatus of claim 10, wherein the guidewire is secured to the fixator catheter when the fixator is in the expanded configuration.

12. A medical apparatus according to claim 10, wherein the compressible portion of the fixator catheter is compressible to secure the guidewire to the fixator catheter.

13. A medical apparatus according to claim 10, wherein the compressible portion of the fixator catheter is compressed around the guidewire responsive to inflation of the balloon.

14. A method for delivering a medical apparatus, comprising:
providing a fixator catheter comprising a tubular body with a distal portion and a proximal portion, wherein a lumen extends through the tubular body of the fixator catheter including the distal and proximal portions thereof, and further wherein the lumen terminates at a distal opening at a distal end of the fixator catheter;
passing a guidewire through a body opening of a fixator catheter, through a portion of the tubular body at the distal portion of the fixator catheter, and through the distal opening of the fixator catheter terminating the lumen extending through the tubular body of the fixator catheter, wherein the body opening is defined through a portion of the tubular body of the fixator catheter to the lumen extending through the tubular body of the fixator catheter, and wherein at least a portion of the body opening is defined through the tubular body of the fixator catheter at the distal portion thereof, a fixator being secured to the distal portion of the fixator catheter;
navigating the guidewire to a desired site;
navigating the fixator catheter to the desired site, wherein the guidewire and the fixator catheter are in communication at the distal portion of the fixator catheter with at least a portion of the guidewire extending through and within a portion of the tubular body of the fixator catheter while the guidewire is separate and outside of the tubular body of the fixator catheter at the proximal portion of the fixator catheter;
expanding the fixator to an expanded configuration to releasably secure a portion of the guidewire to the fixator catheter in the lumen within the portion of the tubular body at the distal portion of the fixator catheter and releasably secure the fixator catheter, and the guidewire secured thereto, within a blood vessel; and
advancing an implantable electrically conductive lead of a cardiac device over the guidewire that is separate and outside of the tubular body of the fixator catheter at the proximal portion of the fixator catheter toward the body opening while the fixator is deployed.

15. The method of claim 14, further comprising:
contracting the fixator to a compact configuration to release the fixator catheter; and
removing the guidewire and fixator catheter from the desired site.

16. The method of claim 14, wherein the guidewire is secured to the fixator catheter in the expanded configuration.

17. The method of claim 14, wherein the guidewire is movable in relation to the fixator catheter in the compact configuration.

18. The method of claim 14, wherein the fixator comprises an inflatable balloon comprising etched surface fixation formations.

19. The method of claim 14, wherein the fixator comprises an inflatable balloon comprising a helical or spiral configuration for following a tortuous path.

20. The method of claim 14, wherein the fixator comprises a mechanical anchor having deployable parts.

21. The method of claim 20, wherein the deployable parts comprise movable wings.

22. The method of claim 20, wherein the fixator comprises a pinwheel.

23. The method of claim 14, further comprising:
contracting the fixator to a compact configuration to release the fixator catheter;
removing the guidewire from the fixator catheter;
expanding the fixator to the expanded configuration to releasably secure the implantable electrically conductive lead;
adjusting the guidewire within the desired site;
contracting the fixator to the compact configuration to release the implantable electrically conductive lead;
expanding the fixator to the expanded configuration to releasably secure the guidewire and fixator catheter; and
adjusting the implantable electrically conductive lead within the desired site.

24. The method of claim 14, further comprising:
navigating a delivery catheter adjacent the desired site; and
removing the delivery catheter from adjacent the desired site without slitting the delivery catheter.

25. The method of claim 24, wherein removing the delivery catheter occurs while the fixator is in the expanded configuration.

26. The method of claim 24, wherein removing the delivery catheter comprises removing the delivery catheter prior to advancing the implantable electrically conductive lead toward the body opening over the guidewire.

27. The method of claim 14, wherein the body opening is defined through the tubular body of the fixator catheter proximate the fixator.

28. A method for delivering a medical apparatus, comprising:
providing a fixator catheter comprising a tubular body with a distal portion and a proximal portion, wherein a lumen extends through the tubular body of the fixator catheter including the distal and proximal portions thereof, and further wherein the lumen terminates at a distal opening at a distal end of the fixator catheter;
passing a guidewire through a body opening of a fixator catheter, through portion of the tubular body at the distal portion of the fixator catheter, and through the distal opening of the fixator catheter terminating the lumen extending through the tubular body of the fixator catheter, wherein the body opening is defined through a portion of the tubular body of the fixator catheter to the lumen extending through the tubular body of the fixator catheter, and wherein at least a portion of the body opening is defined through the tubular body of the fixator catheter at the distal portion thereof, a fixator being secured to the distal portion of the fixator catheter and the body opening being arranged between the fixator and the proximal portion;
navigating the guidewire to a desired site;
navigating the fixator catheter to the desired site, wherein the guidewire and the fixator catheter are in communication at the distal portion of the fixator catheter with at least a portion of the guidewire extending through and within a portion of the tubular body of the fixator catheter while the guidewire is separate and outside of the tubular body of the fixator catheter at the proximal portion of the fixator catheter;

expanding the fixator to an expanded configuration to releasably secure a portion of the guidewire to the fixator catheter in the lumen within the portion of the tubular body at the distal portion of the fixator catheter and releasably secure the fixator catheter, and the guidewire secured thereto, within a blood vessel; and advancing an implantable electrically conductive lead of a cardiac device over the guidewire that is separate and outside of the tubular body of the fixator catheter at the proximal portion of the fixator catheter toward the body opening while the fixator is deployed;

wherein the fixator comprises an inflatable balloon and the guidewire passes through a compressible portion of the fixator catheter within the inflatable balloon.

29. The method of claim 28, wherein the guidewire is secured to the fixator catheter when the fixator is in the expanded configuration.

* * * * *